United States Patent [19]

Bär et al.

[11] 4,356,306

[45] Oct. 26, 1982

[54] WATER-SOLUBLE DERIVATIVES OF 6,6'-METHYLENE-BIS-(2,2,4-TRIMETHYL-1,2-DIHYDROQUINOLINE)

[75] Inventors: Vilmos Bär; Joszef Böszörmenyi; Péter Richter; Jenö Mercz; Tamás Rozsnyai, all of Budapest, Hungary

[73] Assignees: Material Vegyipari Szovetkezet; Human Oltoanyagtermelo es Kutato Intezet, both of Budapest, Hungary

[21] Appl. No.: 164,526

[22] Filed: Jul. 2, 1980

[30] Foreign Application Priority Data

Jul. 6, 1979 [HU] Hungary .............................. MA 3172

[51] Int. Cl.$^3$ ........................................... C07D 215/12
[52] U.S. Cl. ..................................... 546/176; 424/258
[58] Field of Search ......................... 546/176; 424/258

[56] References Cited

U.S. PATENT DOCUMENTS 3,047,521 7/1962 Harman ....................... 260/45.8 W
4,025,631 5/1977 Bar et al. .............................. 424/258

*Primary Examiner*—David B. Springer
*Attorney, Agent, or Firm*—Karl F. Ross

[57] ABSTRACT

The invention relates to water-soluble alkali salts of mono- and disulfonic acid derivatives and mono- and disulfonamide derivatives of 6,6'-methylene-bis-(2,2,4-trimethyl-1,2-dihydroquinoline) and dimer and/or trimer condensation products thereof bound with a methylene bridge at the 8 or 8' position. The new compounds are radioprotective and radiosensibilizers at the same time, and may be used both in the therapy and prophylaxis of malignant tumors.

5 Claims, No Drawings

WATER-SOLUBLE DERIVATIVES OF 6,6'-METHYLENE-BIS-(2,2,4-TRIMETHYL-1,2-DIHYDROQUINOLINE)

The present invention relates to water-soluble derivatives of 6,6'-methylene-bis(2,2,4-trimethyl-1,2-dihydroquinoline) (MTDQ) and dimer and/or trimer condensation products thereof as well as processes for the preparation of the above products. More specifically the invention is concerned with the alkali metal salts of mono- and disulfonic acid derivatives and mono- and disulfonamide derivatives of MTDQ and dimer and/or trimer condensation products thereof, and processes for the preparation thereof. The term "dimer" as used herein stands for molecules consisting of three isoquinoline units which are connected by methylene bridges while "trimer" refers to units of four isoquinolines connected by methylene bridges.

It has been disclosed in Hungarian Pat. No. 162 358 and German Pat. No. 2 243 777 and U.S. Pat. No. 4,025,631 that 6,6'-methylene-bis(2,2,4-trimethyl-1,2-dihydroquinoline) and dimer and trimer derivatives thereof (referred to hereinafter as MTDQ including dimer and trimer derivatives thereof) increase the radiosensibility of malignant tumor tissues and may be successfully employed in the therapy of radio-insensitive tumors or tumors which are not sufficiently radiosensitive. With MTDQ radiosensitive tumors may be treated with a reduced radiodose (by at least 50%) and the same effect is achieved. Therapeutic activity and toxicity of MTDQ are disclosed in the following references: Pollak et al.: Strahlentherapie 154. (1978) 499–502 Nr. 2; Pollak et al.: Acta Radiologica Oncology 18 (1979) Fasc. 2. 97–102; Erdelyi et al.: Strahlentherapie 156 (1980) 198–200 Nr. 3; Hall et al.: Radiation Oncology Biol. Phys. Vol. 5. (1979) 1781–1786.

In order to increase the efficiency of radiotherapy new possibilities have been sought. A new active ingredient is needed which may be employed simultaneously as a radioprotects agent selectively protecting the healthy tissues and as a radiosensitizer acting on the hypoxaemic cells, but the collective toxicity of the radioprotective and radiotherapeutic active ingredients should not be additive. (J. D. Chapman and R. C. Urtasum: Cancer, 1977, July Supplement, 40, 486.)

We have now found that the alkali metal salts of mono- and disulfonic acid and mono- and disulfonamide derivatives of MTDQ possess an extremely high radioprotective activity and at the same time when administered continuously for a long time alone or combined with radiosensitizers, which act selectively on hypoxaemic cells, they possess outstanding therapeutic and prophylactic properties. Due to these properties the above-mentioned compounds can effectively be used in the treatment and prophylaxis of malignant tumors.

The invention relates to compounds of the formula I

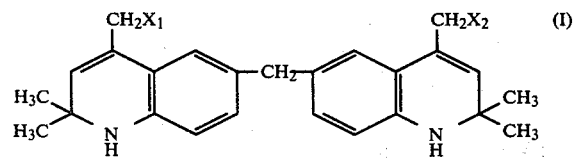

wherein $X_1$ and $X_2$ are each hydrogen, $-SO_3Me$ or $-SO_2NH_2$, wherein Me is an alkali metal atom, preferably sodium,
with the proviso that $X_1$ or $X_2$ is always different from hydrogen—and to dimer and/or trimer condensation products thereof bound with a methylene bridge between the carbon atom at the position 8 or 8' of the ring.

The invention also provides a process for the preparation of the compounds of the formula I and dimer and trimer condensation products thereof.

According to the invention the compounds of the formula I may be prepared by (a) sulfonating 6,6'-methylene-bis(2,2,4-trimethyl-1,2-dihydroquinoline) and/or dimer and/or trimer condensation products thereof bound with a methylene bridges between the carbon atom at the position 8 or 8'0 of the ring, with one or two molar equivalents of concentrated sulfuric acid or oleum or reacting same with chlorosulfonic acid to give sulfochloride e.g. in the presence of a solvent such as an excess of the sulfonating agent; or (b) condensing 2,2-dimethyl-4-methane-sulfonic acid-1,2-dihydroquinoline with 0.5 to 0.6 mole of formaldehyde and converting the thus obtained mono- or disulfonic acid or sulfochloride derivative into an alkali metal salt of the corresponding sulfonic acid or to sulfonamide by methods known per se.

The starting material of process variant (a) i.e. 6,6'-methylene-bis(2,2,4-trimethyl-1,2-dihydroquinoline) is a known compound, the preparation of which is disclosed in Hungarian Pat. No. 162 385, German Pat. No. 2 243 777 and U.S. Pat. No. 4,025,631.

Similarly, 2,2-dimethyl-4-methane-sulfonic acid-1,2-dihydroquinoline is also a known compound (J. Cliffe: J. Chem. Soc., 1933, 1327–1331) and the first step of the synthesis using this compound as starting material is disclosed in Hungarian Pat. No. 162 358.

The salts may be prepared by methods known per se. Thus for example, sodium salt may be prepared by reacting the sulfonic acid with sodium hydroxide, but in order to get a pure product one may first prepare the water soluble calcium or barium salt of the sulfonic acid followed by a reaction with sodium carbonate. The obtained product may also be purified by recrystallization from water or a mixture of alcohol and water.

Mono- or disulfonamide may preferably be prepared by reacting mono- or disulfochloride with ammonia but other known amination processes may also be employed.

The invention also extends to pharmaceutical compositions containing as active ingredient the new compounds of the formula I and or dimer- and/or trimer-derivatives thereof.

The compounds can be formulated into pharmaceutical compositions which are suitable for oral or parenteral route of administration. The compositions comprise one or more compounds of the formula I as active ingredient and/or dimer and/or trimer derivatives thereof and pharmaceutically acceptable inert carriers and/or diluents and optionally other conventionally used excipients.

The efficiency of the compounds of the invention was investigated in vitro by measuring the inhibitor activity of the compounds on the polymerization of acrylic acid at 60° C., and comparing this activity with that of 3.5-di-tert.butyl-4-hydroxy-toluene (BHT) and L-ascorbic acid. The radical binding activity of the compounds was studied.

The times required to polymerization are given in the next Table.

|  | hours |
|---|---|
| Control | 16 |
| BHT 0.02% | 120 |
| L-ascorbic acid 0.02% | 18 |
| MTDQ-disulfonic acid | 400 |

The results of acute toxicity tests in mice show that in a 10 days observation period no death occurred in the case of alkali salts of disulfonic acid and monosulfonic acid or in case of mono- and disulfonamide derivatives at a single dose of 5 g./kg. i.e. $LD_{50}$ value is higher than 5 g./kg., i.p. administration at a dose of 3 g./kg. caused no death. The 90 days toxicity test showed no toxicity at a dose of 250 mg./kg. body-weight.

The unexpected activity of the new compounds has been observed during a total body irradiation. As test animals CFLP mice of an average weight of 20 to 22 g. were used, each group consisted of 8 male and 8 female animals. The control group was irradiated with 7 Gy (total body irradiation) and the test groups were treated per os for 10 days with the new water-soluble antioxidant of the invention at a daily dose of 0.5 g./kg. The treatment was followed by 7 Gy total body irradiation. There was no significant difference between the various water-soluble antioxidants and as a result within 30 days two animals of the control group were alive and an average of 12 animals survived in the treated group. A significant result was obtained with $X^2$ probe, $p<0.001$ and the Dose Modification Factor (DMF), which is the number of dead animals in the control group related to the number of dead animals in the treated group, amounted to 3.5 at $LD_{80}$. A dose of 1000 mg./kg. body-weight of MTDQ disulfonic acid Na was administered i.p. preferably 2 hours before irradiation with an $LD_{90}$ radiodose and a 100% protective activity was obtained. This unexpected result is important per se, as the known radioprotective compounds, such as cysteine, cysteamine (beta-mercapto-ethyl-amine), AET (S-2-amino-ethyl-isothiuronium-dihydrobromide) and S-2-(3-aminopropyl)-aminoethyl-phosphorothioic acid (WR 2721) are effective only at subtoxic doses and their duration of effect after administration is also extremely limited. It is known that the radioprotective compounds protect the healthy tissue cells better than the malignant tumor cells.

The new compounds according to the invention possess a further advantage, the plasma concentration of the water-soluble antioxidant is higher (by an order of magnitude) than that of MTDQ. When investigating the plasma concentration, MTDQ was also found in the plasma along with the undecomposed compound, probably as a first metabolite thereof, which was formed by desulfonation.

The concentration of the found MTDQ was the same as if it had not been the compound of the invention that had been administered, but rather MTDQ. MTDQ could be detected in the liver as well. The radioprotective activity of the water-soluble antioxidant is presumably due to the fact that the radiation energy is predominantly concentrated on the antioxidant and further that in addition to its membrane stabilizing activity the radicals and peroxides formed in the course of the irradiation, are inactivated by the antioxidant, in the well oxygenated cells.

A further advantage of the new sulfonated derivatives may be seen in their radioprotective activity in the healthy cells and in the simultaneous radiosensitizing activity of the MTDQ derived from the sulfonated derivatives in hypoxaemic cells, mainly during a long-lasting continuous administration. Thus the new derivatives may be used in the treatment of all the tumors which could be successfully treated with MTDQ. The concentration of the free radicals and peroxides which may be detected by electrospin resonancy (ESR), gradually increases until the half-life of the tumor growth, as well as in metastasis.

The surrounding carcinogens play an important role in the formation of malignant tumors. These carcinogens contain free radicals or they become carcinogenic in the living organism. Thus it can be expected that antioxidants inactivating the free radicals possess anticarcinogenic activity. As the radical reactions may be controlled by the antioxidants, they may be employed as therapeutic and as prophylactic agents as well. This was proved by the following model. A hepatotoxic substance had to be administered which was simultaneously carcinogenic. Dimethylsulfoxide was suitable. 0.3 ml. of dimethylsulfoxide/mice was administered i.p. or s.c. in an aqueous solution and as a result 7 animals died within 10 days out of 10 test animals. At the same time 100 mg. of disulfonic acid and 60 mg. of disulfonamide were dissolved or suspended in a mixture of water and the above solvent and the route of administration was i.p. or s.c. As a result no death was observed. i.e. the protective activity was 100%. The mechanism of activity of the antioxidant in man has not been completely clarified yet but there is data available to prove their tumor inhibiting activity. In the presence of a large amount of Vitamin-C beta-naphthyl-amine does not cause cancer of the bladder and in those countries where antioxidants are used as food additives, the number of the patients having cancer of the stomach or colon and the death rate decrease. The highly active synthetic antioxidants which have been hitherto known may not be employed for pharmaceutical purposes due to their toxicity and unfavorable pharmacokinetic properties. A water-soluble and non-toxic highly active antioxidant is suitable for therapeutic and prophylactic purposes, when administered per os or parenterally, in the case of all carcinogens or precursors, such as benzpyrene, dimethylbenzanthracene, precursors of carcinogenic nitroso-amines etc., wherein free radical reactions take place.

The antioxidants inhibit the degradation of cholesterine, and thus may be used in the treatment of atheroeclerosis and various heredodegenerative diseases (such as Spiermeyer-Vogt disease, or certain types of haemolytic anaemia of new-borns), liver cirrhosis, where free radical reactions could be detected or such reactions occur in the pathogenesis thereof.

The compounds of the invention thus also reduce or eliminate radiation injury when administered 30 minutes to 6 hours after radiation. When administered to neonatal rats before being introduced into the incubator the compounds eliminate the toxic oxygen effect.

Details of the invention may be found in the following Examples which serve merely for illustration and not for limitation.

EXAMPLE 1

358 g. of 6,6'-methylene-bis(2,2,4-trimethyl-1,2-dihydroquinoline) are dissolved in 1000 g. of 96% sulfuric acid and the mixture is kept at 80° to 95° C. under stirring until a clear solution is obtained. The reaction mixture is then poured to a saturated aqueous sodium chloride solution. The mixture is cooled down while 6,6'-methylene-bis(2,2-dimethyl-4-methanesulfonic acid Na-1,2-dihydroquinoline) is precipitated accompanied by a small amount of sodium chloride. In order to obtain a pure product the crude product obtained as described above, is mixed with an aqueous suspension of equimolar calcium hydroxide, the water soluble calcium salt of the disulfonated product is separated by filtration and an aqueous solution of the equimolar sodium carbonate is added to the aqueous solution. The precipitated calcium carbonate is filtered off and 6,6'-methylene-bis(2,2-dimethyl-4-methane sulfonic acid Na-1,2-dihydroquinoline) is isolated after evaporation of the aqueous solution. The product may, if desired, be recrystallized from a 1:1 V/V mixture of water and methanol.

Yield: 505 g.

Analysis: Calculated: molecular weight: 562, S: 11.38%. Found: molecular weight: 559, S: 10.82%.

EXAMPLE 2

To a 1.5 liter flask equipped with a stirrer, gas outlet tube, inner thermometer and dropping funnel a solution of 358 g. of 6,6'-methylene-bis(2,2,4-trimethyl-1,2-dihydroquinoline) in 1500 g. of methylene chloride are added. Under external cooling and stirring 350 g. of chlorosulfonic acid are added, while the reaction temperature is maintained at 5° to 20° C. The mixture is then stirred at room temperature until the hydrochloric acid gas evolution ceases, whereafter the reaction mixture is poured on 300 g. of crushed ice and the precipitated 6,6'-methylene-(2,2-dimethyl-4-methanesulfochloride-1,2-dihydroquinoline-2',2',4'-trimethyl-1',2'-dihydroquinoline is filtered by suction.

365 g. of crude monosulfochloride obtained as disclosed above are boiled with a 15% aqueous sodium hydroxide solution until the pH is adjusted to 7.2. The precipitated sodium salt of monosulfonic acid is isolated after cooling down and purified through water soluble calcium salt as disclosed in Example 1. Thus 345 g. of 6,6'-methylene-(2,2-dimethyl-4-methanesulfonic acid-Na-1,2-dihydroquinoline-2',2',4'-trimethyl-1',2'-dihydroquinoline) are obtained.

EXAMPLE 3

365 g. of 6,6'-methylene-(2,2-dimethyl-4-methanesulfochloride-1,2-dihydroquinoline-2',2',4'-trimethyl-1',2'-dihydroquinoline) obtained according to Example 2 are dissolved in 500 ml. of water and 300 ml. of a 20% aqueous ammonium hydroxide solution are added under stirring and the mixture is heated to 70° C. 6,6'-methylene-(2,2-dimethyl-4-methanesulfonamide-1,2-dihydroquinoline-2',2',4'-trimethyl-1',2'-dihydroquinoline is precipitated under cooling. The product is filtered by suction and recrystallized from a 1:1 V/V mixture of water and ethanol. Yield 315 g. Molecular weight determined by obullioscopy:437 (calculated 441).

We claim:

1. A 6,6'-Methylene-bis(2,2,4-trimethyl-1,2-dihydroquinoline) compound of the formula I

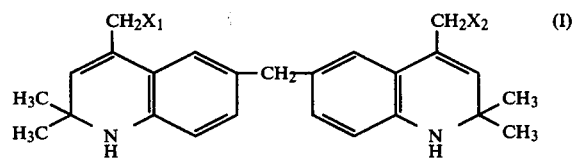

wherein $X_1$ and $X_2$ stand for hydrogen, —$SO_3Me$ or —$SO_2NH_2$— wherein Me represents an alkali metal atom, but that one of $X_1$ and $X_2$ is always different from hydrogen.

2. A compound as defined in claim 1 wherein in the formula I $X_1$ stands for —$SO_3Me$ or —$SO_2NH_2$, and $X_2$ is hydrogen.

3. A compound as defined in claim 1 wherein in the formula I $X_1$ and $X_2$ stand for —$SO_3Me$ or —$SO_2NH_2$.

4. 6,6'-Methylene-bis(2,2-dimethyl-4-methanesulfonic acid Na-1,2-dihydroquinoline) as defined in claim 1.

5. 6,6'-Methylene-(2,2-dimethyl-4-methanesulfonamide-1,2-dihydroquinoline-2',2',4'-trimethyl-1',2'-dihydroquinoline) as defined in claim 1.

* * * * *